US009322804B2

(12) United States Patent
Whitesides et al.

(10) Patent No.: US 9,322,804 B2
(45) Date of Patent: Apr. 26, 2016

(54) QUALITY CONTROL OF DIAMAGNETIC MATERIALS USING MAGNETIC LEVITATION

(75) Inventors: George M. Whitesides, Cambridge, MA (US); Audrey Ellerbee, Stanton, CA (US); Simon Tricard, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 196 days.

(21) Appl. No.: 13/989,725

(22) PCT Filed: Nov. 29, 2011

(86) PCT No.: PCT/US2011/062399
§ 371 (c)(1),
(2), (4) Date: Aug. 12, 2013

(87) PCT Pub. No.: WO2012/075009
PCT Pub. Date: Jun. 7, 2012

(65) Prior Publication Data
US 2013/0314080 A1 Nov. 28, 2013

Related U.S. Application Data

(60) Provisional application No. 61/417,774, filed on Nov. 29, 2010.

(51) Int. Cl.
G01N 27/72 (2006.01)
G01R 33/12 (2006.01)

(52) U.S. Cl.
CPC ............ *G01N 27/72* (2013.01); *G01R 33/1269* (2013.01); *G01R 33/1276* (2013.01)

(58) Field of Classification Search
CPC ....... H02N 15/00; G01N 27/72; G01N 27/82; G01N 27/825; G01R 33/1276; G01R 33/12

USPC .................................. 324/232, 228; 73/432.1
See application file for complete search history.

(56) References Cited

U.S. PATENT DOCUMENTS 4,049,398 A 9/1977 Vaseen
4,062,765 A 12/1977 Fay et al.
(Continued)

FOREIGN PATENT DOCUMENTS

EP 0571858 A1 12/1993
WO WO-2005085131 A2 9/2005
(Continued)

OTHER PUBLICATIONS

Beaugnon, et al., "Levitation of Organic Materials," Nature, vol. 349, Feb. 1991, pp. 470.
(Continued)

*Primary Examiner* — Tung X Nguyen
*Assistant Examiner* — Robert P Alejnikov, Jr.
(74) *Attorney, Agent, or Firm* — Wilmer Cutler Pickering Hale and Dorr LLP

(57) ABSTRACT

The ability to levitate and detect height and orientation of diamagnetic objects suspended in paramagnetic solutions using an inhomogeneous magnetic field is described. By comparing the measured height and orientation of a sample material with the measured height and orientation of a reference material, quality control of objects can be carried out. The major advantages of this quality control technique are: i) it is a simple apparatus that does not require electric power (a set of permanent magnets and gravity are sufficient for the diamagnetic separation and collection system to work); ii) it is compatible with simple optical detection; iii) it is a cost-effective and simple method that can carry out quality control between sample and reference materials rapidly.

10 Claims, 5 Drawing Sheets

(56) References Cited

U.S. PATENT DOCUMENTS

| | | | |
|---|---|---|---|
| 4,957,939 A | 9/1990 | Gries et al. | |
| 5,146,566 A * | 9/1992 | Hollis et al. | 710/73 |
| 6,902,065 B2 | 6/2005 | Kimura et al. | |
| 7,008,572 B2 | 3/2006 | Kimura et al. | |
| 2002/0022276 A1 | 2/2002 | Zhou et al. | |
| 2002/0153295 A1 | 10/2002 | Kimura et al. | |
| 2002/0197622 A1 | 12/2002 | McDevitt et al. | |
| 2003/0219785 A1 | 11/2003 | Hallahan et al. | |
| 2004/0009614 A1 | 1/2004 | Ahn et al. | |
| 2004/0072278 A1 | 4/2004 | Chou et al. | |
| 2005/0274650 A1 | 12/2005 | Frazier et al. | |
| 2007/0194227 A1* | 8/2007 | Dolan | 250/309 |
| 2009/0184595 A1* | 7/2009 | Farber | 310/90.5 |
| 2010/0253328 A1* | 10/2010 | Celedon et al. | 324/207.25 |
| 2010/0285606 A1* | 11/2010 | Phillips et al. | 436/501 |
| 2011/0008646 A1* | 1/2011 | Cahalen et al. | 428/655 |
| 2011/0018532 A1* | 1/2011 | Florescu et al. | 324/251 |

FOREIGN PATENT DOCUMENTS

| | | | |
|---|---|---|---|
| WO | WO-2005105314 A1 | 11/2005 | |
| WO | WO-2007035498 A2 | 3/2007 | |
| WO | WO2009006409 * | 1/2009 | G01N 33/53 |
| WO | WO-2009006409 A2 | 1/2009 | |

OTHER PUBLICATIONS

Blackledge, Robert D., "Forensic Analysis on the Cutting Edge: New Methods for Trace Evidence Analysis," Wiley Interscience, Chapter 1 and Chapter 10, 102 pages (2007).

Brandt, E. H., "Levitation in Physics," Science, vol. 243, No. 4889, Jan. 1989, pp. 349-355.

Catherall, et al., "Cryogenically Enhanced Magneto-Archimedes Levitation," New Journal of Physics, 7, 2005, 118, 10 pages.

Catherall, et al., "Floating Gold in Cryogenic Oxygen," Nature, vol. 422, Apr. 2003, pp. 579.

Catherall, et al., "Separation of Binary Granular Mixtures Under Vibration and Differential Magnetic Levitation Force," Physical Review E 71, 2005, pp. 021303-1-021303-8.

Chetouani, H. et al., "Diamagnetic Levitation of Beads and Cells Above Permanent Magnets," IEEE, Transducers & Eurosensors '07, The 14th International Conference on Solid-State Sensors, Actuators and Microsystems, Lyon, France, 4 pages (Jun. 10-14, 2007).

Choi, et al., "An Integrated Microfluidic Biochemical Detection System for Protein Analysis with Magnetic Bead-Based Sampling Capabilities," Lab Chip, 2002, 2, pp. 27-30.

Feinstein, et al., "Three-Dimensional Self-Assembly of Structures Using the Pressure Due to a Ferrofluid in a Magnetic Field Gradient," Journal of Applied Physics 99, 2006, pp. 064901-1-064901-6.

Franzreb, et al., "Protein Purification Using Magnetic Adsorbent Particles," Appl. Microbiol. Biotechnol., 2006, 70, pp. 505-516.

Furdui, et al., "Immunomagnetic T Cell Capture from Blood for PCR Analysis Using Microfluidic Systems," Lab Chip, 2005, 4, pp. 614-618.

Gates, et al., "New Approaches to Nanofabrication: Molding, Printing, and Other Techniques," Chem. Rev., 2005, 105, pp. 1171-1196.

Geim, et al., "Magnet Levitation at your Fingertips," Nature, vol. 400, Jul. 1999, pp. 323-324.

Gijs, M., "Magnetic Bead Handling On-Chip: New Opportunities for Analytical Applications," Microfluid Nanofluid, 2004, 1, pp. 22-40.

Haukanes, et al., "Application of Magnetic Beads in Bioassays," Bio/Technology, vol. 11, Jan. 1993, pp. 60-63.

Hirota, et al., "Magneto-Archimedes Levitation and its Application," RIKEN Review No. 44, Feb. 2002, pp. 159-161.

Hirota, et al., "Magneto-Archimedes Separation and Its Application to the Separation of Biological Materials," Physica B 346-347, 2004, pp. 267-271.

Ikezoe, et al., "Making Water Levitate," Nature, vol. 393, Jun. 1998, pp. 749-750.

Ikezoe, et al., "Separation of Feeble Magnetic Particles with Magneto-Archimedes Levitation," Energy Conversion and Management 43, 2002, pp. 417-425.

Ikezoe, et al., "Stable Levitation of Water by Magneto-Archimedes Principle," Transactions of the Materials Research Society of Japan, 2000, 25 [1], pp. 77-80.

Inglis, et al., "Microfluidic High Gradient Magnetic Cell Separation," Journal of Applied Physics 99, 2006, pp. 08K101-1-08K101-3.

International Search Report and Written Opinion of the International Searching Authority, the United States Patent and Trademark Office, for International Application No. PCT/US2008/068797, dated Dec. 31, 2008, 13 pages.

Islam et al., "Detection of Shigella dysenteriae Type 1 and Shigella flexneri in Feces by Immunomagnetic Isolation and Polymerase Chain Reaction," Journal of Clinical Microbiology, vol. 30, No. 11, Nov. 1992, pp. 2801-2806.

Ito, et al., "Review: Medical Application of Functionalized Magnetic Nanoparticles," Journal of Bioscience and Bioengineering, vol. 100, No. 1, 2005, pp. 1-11.

Jayawant, B. V., "Electromagnetic Suspension and Levitation," Rep. Prog. Phys., vol. 44, 1981, pp. 411-477, 74 pages.

Jayawant, B. V., "Review Lecture: Electromagnetic Suspension and Levitation Techniques," Proc. R. Soc. Lond., A 416, pp. 245-320, Apr. 1988.

Kimura, "Study on the Effect of Magnetic Fields on Polymeric Materials and Its Application," Polymer Journal, vol. 35, No. 11, pp. 823-843, 2003.

Kimura, et al., "Micropatterning of Cells Using Modulated Magnetic Fields," Langmuir 2005, 21, pp. 830-832.

Kimura, et al., "Separation of Solid Polymers by Magneto-Archimedes Levitation," Chemistry Letters 2000, pp. 1294-1295.

Lee, et al., "Solvent Compatibility of Poly(dimethylsiloxane)-Based Microfluidic Devices," Anal. Chem., 2003, 75, pp. 6544-6554.

Lockett, M.R. et al., "Density Detennination via Magnetic Levitation," The CACNews, pp. 20-21, 4 pages, 3rd Quarter 2011.

Lund et al., "Assessment of Methods for Covalent Binding of Nucleic Acids to Magnetic Beads, Dynabeads™, and the Characteristics of the Bound Nucleic Acids in Hybridization Reactions," Nucleic Acids Research, vol. 16, No. 22, 1988, pp. 10861-10880.

Lyuksyutov, et al., "Trapping Microparticles with Strongly Inhomogeneous Magnetic Fields," Midern Physics Letters B., vol. 17, No. 17, 2003, pp. 935-940.

McCarty, et al., "Self-Assembly: Electrostatic Self-Assembly of Polystyrene Microspheres by Using Chemically Directed Contact Electrification," Agnew. Chem. Int. Ed., 2007, 46, pp. 206-209.

Meldal et al., "Direct Visualization of Enzyme Inhibitors using a Portion Mixing Inhibitor Library Containing a Quenched Fluoregenic Peptide Substrate. Part 1. Inhibitors for Subtilisin Carlsberg," J. Chem. Soc. Perkin Trans., Jan. 1995, pp. 1591-1596.

Ng, et al., "Review: Components for Integrated Poly(dimethylsiloxane) Microfluidic Systems," Electrophoresis, 2002, 23, pp. 3461-3473.

Oberteuffer, J., "Magnetic Separation: A Review of Principles, Devices, and Applications," IEEE Transactions on Magnetics, vol. MAG-10, No. 2, Jun. 1974, pp. 223-238.

Pamme, et al., "On-Chip Free-Flow Magnetophoresis: Continuous Flow Separation of Magnetic Particles and Agglomerates," Anal. Chem., 2004, 76, pp. 7250-7256.

Pamme, N., "Magnetism and Microfluidics," Lab Chip, 2006, pp. 24-38.

Purcell, E., "Electricity and Magnetism," Berkeley Physics Course, vol. 2, Second Edition, ISBN 0-07-004908-4, 497 pages (1985).

Raj, et al., "Invited Paper: Commercial Applications on Ferrofluids," Journal of Magnetism and Magnetic Materials, 85, 1990, pp. 233-245.

Raj, et al., "New Commercial Trends of Nanostructured Ferrofluids," Indian Journal of Engineering & Materials Sciences, vol. 11, Aug. 2004, pp. 241-252.

Safarik et al., "Review: Use of Magnetic Techniques for the Isolation of Cells," Journal of Chromatography B,. 722, 1999, pp. 33-53.

Shipway, et al., "Investigations into the Electrostatically Induced Aggregation of Au Nanoparticles," Langmuir, 2000, 16, pp. 8789-8795.

(56) References Cited

OTHER PUBLICATIONS

Sia, et al., "Analytical Methods: An Integrated Approach to a Portable and Low-Cost Immunoassay for Resource-Poor Settings," Agnew. Chem. Int. Ed., 2004, pp. 498-502.

Simon, et al., "Diamagnetic Levitation: Flying Frogs and Floating Magnets (invited)," Journal of Applied Physics, vol. 87, No. 9, May 2000, pp. 6200-6204.

Squires, et al., "Microfluidics: Fluid Physics at the Nanoliter Scale," Reviews of Modern Physics, vol. 77, Jul. 2005, pp. 977-1026.

Supplemental European Search Report and Written Opinion for European Patent Application No. 08826080 dated Jan. 25, 2011, 14 pages.

Watarai et al., "Magnetophoretic Fractionation of Microparticles in Aqueous Media in Capillary Flow System," Analytical Sciences, vol. 17 Supplement, pp. i169-i171, 3 pages (2001).

Watarai, et al., "Capillary Magnetophoresis of Human Blood Cells and their Magnetophoretic Trapping in a Flow System," Journal of Chromatography A, 961, 2002, pp. 3-8.

Watarai, et al., "Magnetophoretic Behavior of Single Polystyrene Particles in Aqueous Manganese(II) Chloride," Analytical Sciences, Oct. 2001, vol. 17, pp. 1233-1236.

Weibel, et al., "Bacterial Printing Press that Regenerates its Ink: Contact-Printing Bacteria Using Hydrogel Stamps," Langmuir, 2005, 21, pp. 6436-6442.

Winkleman, et al., "A Magnetic Trap for Living Cells Suspended in a Paramagnetic Buffer," Applied Phuysics Letters, vol. 85, No. 12, Sep. 2004, pp. 2411-2413.

Xia, et al., "Soft Lithography," Agnew. Chem. Int. Ed., 1998, 28, pp. 551-575.

Yager, et al., "Microfluidic Diagnostic Technologies for Global Public Health," Nature, vol. 442, Jul. 2006, pp. 412-418.

Yamato, Novel Strategies for Fundamental Innovation in Polymer Science, 2005, pp. 123-139, ISBN: 81-308-0060-8, Published by Research Signpost, Editor Naofumi Naga.

Yamato, et al., "Levitation Polymerization to Fabricate a Large Polymer Sphere," Langmuir 2002, 18, pp. 9609-9610.

Yellen, B.B. et al., "Arranging matter by magnetic nanoparticle assemblers," PNAS, Vo. 102, No. 25, 5 pages (Jun. 21, 2005).

* cited by examiner

QUALITY CONTROL OF DIAMAGNETIC MATERIALS USING MAGNETIC LEVITATION

RELATED APPLICATIONS

This application is a national stage application of International Application No.: PCT/US2011/062399, filed Nov. 29, 2011, which claims the benefit of priority of U.S. Ser. No. 61/417,774 filed Nov. 29, 2010, the contents of which are hereby incorporated by reference in their entirety.

GOVERNMENT SUPPORT

This invention was made with government support under W911NF-08-1-0143 awarded by U.S. Department of Defense. The U.S. government has certain rights in this invention.

FIELD OF THE INVENTION

Quality control of components using magnetic levitation (MagLev) is described. In particular, quality of control of components using MagLev based on both the levitation position and orientation is described.

BACKGROUND

In the last decade, the magnetic levitation of diamagnetic materials has become more accessible to standard laboratory facilities, as the early experimental setup consisting of superconducting magnets (>10 T) and a pressurized oxygen atmosphere has been replaced by small rare-earth magnets and aqueous paramagnetic salt solutions. One of the characteristics of magnetic levitation is that there is an equilibrium position in a magnetic field in which an object is stably levitated. When a levitating object in magnetic fields is moved away from a position of equilibrium, a restoration force on the object returns it to equilibrium position. The magnetic susceptibility and the density of the object determine this stable point. Therefore, different substances levitated in the same magnetic field have different equilibrium positions of levitation and can thus be separated.

SUMMARY

In certain embodiments, a method for performing a quality control of a diamagnetic sample material is described. The method can include any one of the following steps: levitating a diamagnetic sample material having a non-uniform density profile in a paramagnetic solution using a magnetic field; measuring the height and orientation of said sample material in the paramagnetic solution; comparing the height and orientation of said sample material to the height and orientation of a reference material; and determining whether differences between height and orientation of the sample material and the height and orientation of the reference material are within a predetermined range.

In the certain embodiments, the method further includes: providing a first paramagnetic solution comprising a paramagnetic material in a solvent; providing a reference material having a reference density and a reference density profile in said first paramagnetic solution; applying a magnetic field to the first paramagnetic solution; and measuring the height and orientation of said reference material in the first paramagnetic solution.

In certain embodiments, the reference material and the sample material have a non-spherical geometry.

In certain embodiments, the reference material and the sample have a spherical geometry with a visual marker to detect orientation in the first and second paramagnetic solutions. In certain embodiments, the second paramagnetic solution may have similar characteristics as the first paramagnetic solution, wherein the measurable characteristics (e.g., concentration, density, magnetic susceptibility, and the like) are no different than, up to, 0%, 0.1%, 0.5%, 1%, 5%, 10%, 15%, 20%, 25%, 30% or even up to 35% from each other in composition.

In certain embodiments, the reference density and the reference density profile of the reference material is known.

In certain embodiments, the sample material includes components from a mechanical device.

In certain embodiments, a plurality of reference materials are provided.

In certain embodiments, the method further includes identifying sample materials that have differences that are greater than the predetermined range as failing the quality control.

In certain embodiments, the method further includes identifying sample materials that have differences that are equal to or smaller than the predetermined range as passing the quality control.

In certain embodiments, the orientations are measured relative to at least one axis of a Cartesian coordinate system.

DETAILED DESCRIPTION

The present disclosure describes various strategies utilizing the levitation height and orientation of a diamagnetic material supported in a paramagnetic fluid under the influence of a magnetic field. The magnetic field and its gradient levitate and orient the objects at particular heights and locations, within a paramagnetic solution, based on the overall density and the local density profile within the object. The final position of the objects in the paramagnetic solution and their orientation is directed by a competition between gravitational forces, magnetic forces, and steric interactions (mechanical forces from physical contact) among and between the objects and the container.

Principles Underlying MagLev

Figure 1:
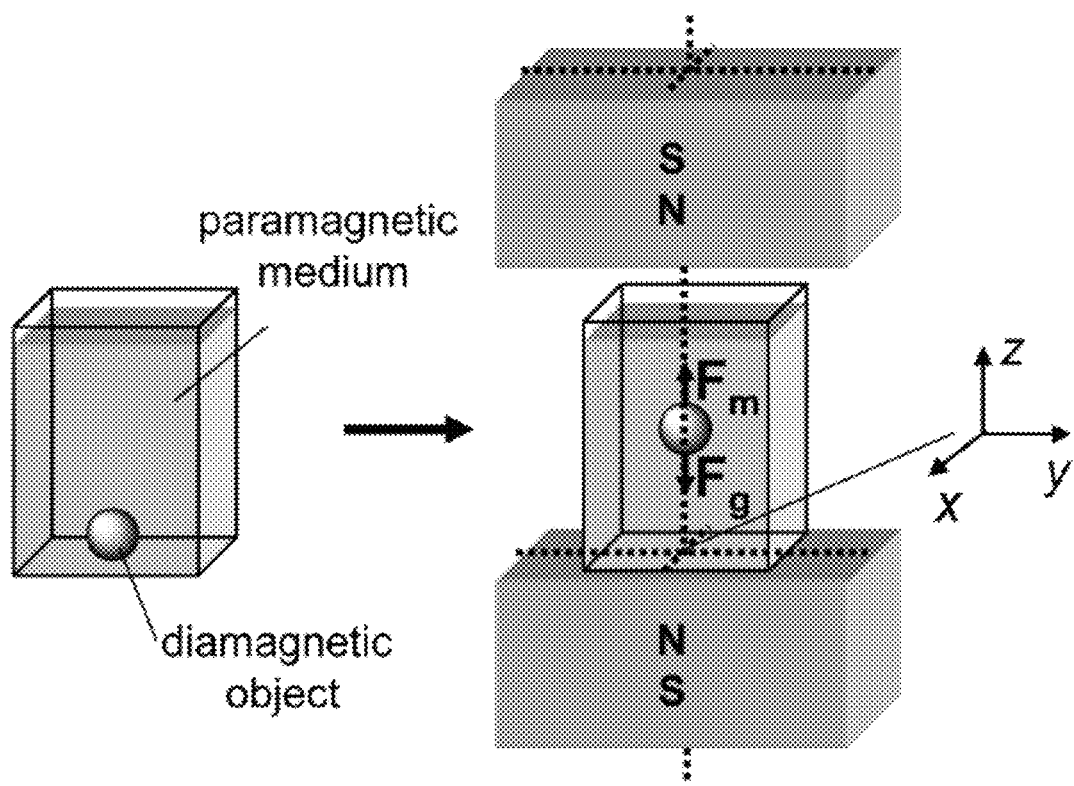
FIG. 1 shows a schematic diagram of magnetic levitation (MagLev) in accordance with certain embodiments.

FIG. 1 summarizes the principles that underlie MagLev. The device used includes two permanent magnets oriented with like poles facing each other (in an anti-Helmholtz configuration), and are separated by a container containing a paramagnetic medium (e.g., an aqueous solution of $MnCl_2$). FIG. 1 shows the balance of magnetic ($F_m$) and gravitational ($F_g$) forces that determines the vertical equilibrium position of an object levitating within the MagLev device. An object whose density is greater than the levitating solution and that would otherwise sink to the bottom of the container outside the magnetic field will float or 'levitate' in the magnetic solution when placed in a magnetic field. Objects that are of non-uniform density will orient in the magnetic field based on the local densities within the object.

The condition of static equilibrium in MagLev for each object can be summarized as follows: i) the net force acting on the object equals zero (Eq. A), and ii) the net torque around any arbitrary pivot point equals zero (Eq. B). In these equations, $F_g(N)$ is the force of gravity, $F_m(N)$ is the magnetic force acting on the object, and r is the lever arm vector (a vector from the pivot point to the point of application of force).

$$\vec{F}_g + \vec{F}_m = \vec{0} \quad (A)$$

$$\vec{r} \times (\vec{F}_g + \vec{F}_m) = \vec{0} \quad (B)$$

To simplify the derivations, an object of heterogeneous density is approximated with a composite object (subscript c) comprising two non-overlapping parts (subscripts a and b) of homogeneous densities whose centers of mass connect by a massless rod of length L(m). (The magnetic susceptibilities of the two parts of the composite object are assumed to be identical). In a 3D Cartesian coordinate system in which the Z-axis is aligned with the direction of the vector of gravity and coincides with the centerline (the line connecting the centers of the two magnets), the origin is in the center of the top surface of the bottom magnet, and the YZ-plane contains the centers of mass of both parts of the composite object. Eq. C gives h(m), the distance between the top surface of the bottom magnet and the center of volume of the object (the "levitation height" of the composite object), and Eq. D gives θ, the angle of tilt of the composite object in the YZ-plane (defined as the angle between the Z-axis and the link connecting the centers of mass of the two components comprising the object).

$$h = \frac{d}{2} + \frac{(\rho_c - \rho_m)g\mu_0}{\alpha_z^2(\chi_c - \chi_m)} \quad (C)$$

$$\theta = \cos^{-1}\frac{(\rho_b - \rho_a)g\mu_0}{(\chi_c - \chi_m)(\alpha_y^2 - \alpha_z^2)L} \quad (D)$$

In these equations, $\rho_a$ (kg/m³) and $\rho_b$ (kg/m³) are the densities of the two parts of the composite object, $\rho_c$ (kg/m³) is the average density of the composite object, $\rho_m$(kg/m³) is the density of the paramagnetic medium, $\chi_c$ (unitless) is the magnetic susceptibility of the object, $\chi_m$ (unitless) is the magnetic susceptibility of the paramagnetic medium, g(m/s²) is the acceleration due to gravity, $\mu_o = 4\pi \times 10^{-7}$ (N/A²) is the magnetic permeability of free space, d(m) is the distance between the magnets, $\alpha_y$ is the gradient of the Z-component of the magnetic field along the Z-axis, B is the magnitude of the magnetic field (A/m), and V is the volume of the sample (m³).

These requirements can be utilized for static equilibrium to organize the components in 3D. The gravitational force acting on an individual component can be controlled by controlling the average density of the component and the density of the fluid, and by patterning the distribution of density within the component. For a particular system with fixed values of magnetic parameters (magnetic field and magnetic field gradient, magnetic susceptibilities) and a medium of constant density, the average density of an object of heterogeneous density determines its levitation height at equilibrium (Eq. C); the pattern of density within the object defines the orientation of the object relative to the axis of gravity (Eq. D). The gradient of magnetic field and the densities of components can be utilized to control the vertical and lateral positions of levitating objects, as well as their orientation.

Quality Control Based on Levitation Height and Orientation

As noted above in Equations (C) and (D), a particular diamagnetic object can achieve an equilibrium height (h) and orientation (θ) in a paramagnetic solution between magnetic fields. Objects of the same shape and made from the same materials, for example, cast, machined or molded objects prepared from the same polymer base, are expected to levitate at the same height and with the same orientation in a magnetic field. It would also be expected that the manufactured objects would have the same density profile. However, variations in the manufacturing process can result in variations in both density and/or density profile. By way of example, air bubbles entrained unintentionally in the polymer base during processing can alter the overall density. Variable processing conditions, differences in shape, undesired residual materials from the manufacturing process (e.g., incomplete removal of release coating during molding) and other events can also lead to variations in the density profile among manufactured objects.

Industry is constantly seeking simple, rapid methods for assessing manufacturing quality and uniformity among manufactured goods and in particular among goods manufactured from batch to batch or over time during continuous processes. MagLev can be used to perform rapid quality control of parts that have been produced.

Figure 2:
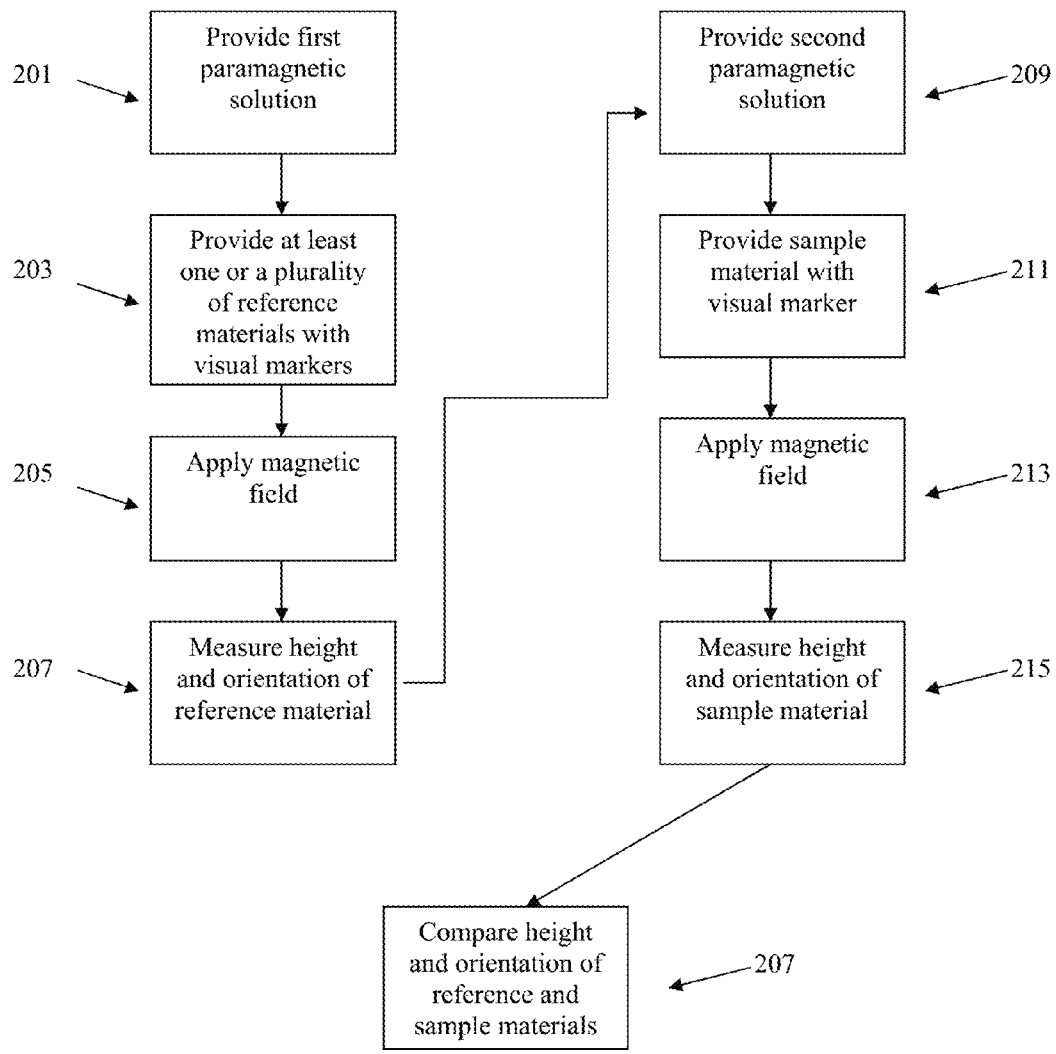
FIG. 2 shows a flow diagram to carry out quality control using MagLev in accordance with certain embodiments.

As shown in FIG. 2, a method of evaluating density characteristics of samples is provided. A first paramagnetic solution that includes a paramagnetic material in a solvent is provided as indicated in step 201. Then, as shown in step 203, a reference material having a known density and density profile (or a reference density and a reference density profile) is introduced into the first paramagnetic solution. In certain embodiments, the reference material can have a non-uniform density profile. In step 205, a magnetic field is applied to the first paramagnetic solution. In step 207, the height and orientation of the reference material in the first paramagnetic solution is measured.

As used herein, a "non-uniform density profile" is meant to describe materials having a density profile so that a torque can be applied to the material upon application of the magnetic field as to induce an observable orientation about at least one axis of the Cartesian coordinate system (e.g., z-axis that is perpendicular to the faces of magnets). For example, the density of the material may change abruptly or gradually or regularly throughout the material to induce an orientation. In certain embodiments, "non-uniform density profile" refers to a material wherein the density is uniform, but the shape of the object is such that an observable orientation can be induced upon application of the magnetic field.

In step 209, a second paramagnetic solution having substantially the same characteristics as the first paramagnetic solution is provided (or the same paramagnetic solution as used for the reference material can be used). In certain embodiments, a stock paramagnetic solution can be used to provide both the first and second paramagnetic solutions. In certain embodiments, the second paramagnetic solution may have substantially the same characteristics as the first paramagnetic solution, wherein the measurable characteristics (e.g., concentration, density, magnetic susceptibility, and the like) are no different than, up to, 0%, 0.1%, 0.5%, 1%, 5%, 10%, 15%, 20%, 25%, 30% or even up to 35% from each other in composition. It should be noted that as described in Equations (C) and (D) above, the levitation height and orientation may depend on the density of the medium, $\rho_m$, and/or the magnetic susceptibility, $\chi_m$. Hence, differences between the first and second paramagnetic solutions may require certain adjustments and/or recalculation of the levitation height and orientation, with larger differences requiring larger adjustments and/or recalculation, as would be apparent to one of ordinary skill in the art. In step 211, a sample material having an unknown density and density profile is introduced into the paramagnetic solution. In certain embodiments, the sample material can have a non-uniform density profile. In step 213, substantially the same magnetic field as that applied in step 205 is applied to the second paramagnetic solution. In step 215, the height and orientation of the sample material in the second paramagnetic solution is measured.

Thereafter, in step 217, the height and orientation of the sample material measured in step 215 is compared to the height and orientation of the reference material measured in step 207. Differences in the material composition (density) of the object are observed as differences in levitation height. Differences in the shape and/or distribution of density in the object are observed as differences in orientation. If the height and orientation are substantially similar, the sample material is accepted as passing a quality control test. If the height and orientation are different, the sample material is rejected as failing a quality control test.

In certain embodiments, one or more of steps 201 to 217 can be carried out sequentially and/or simultaneously. For example, any one of steps 201 and 209; steps 203 and 211; steps 205 and 213; or steps 207 and 215 can be carried out simultaneously. Alternatively, they can be carried out at different times.

In certain embodiments, the reference material's exact density and density profile may not be known. Nevertheless, it may be possible to carry out quality control by comparing the height and orientation of the sample and reference materials, based on whether the height and orientation of the sample and reference materials are substantially similar to each other or not.

In certain embodiments, the two separate paramagnetic solutions may not be needed. For example, in step 207, the height and orientation of the reference material can be recorded via an appropriate means (e.g., software tracking, photographs, videos, etc.). Subsequently, the reference material may be removed from the first paramagnetic solution and the sample material can be introduced into the same first paramagnetic solution to carry out steps 211 through 215. In step 217, the height and orientation recorded in step 207 can be retrieved and compared to the height and orientation recorded in step 215.

In certain embodiments, multiple reference materials can be utilized, each of which may have different heights and/or orientations relative to one another. The multiple reference materials may be representative materials from different classes of objects. For example, each reference material can represent a different production batch, or objects to be colored differently based on density and density profile, unidentified but similarly appearing objects, and the like. After measuring the sample material's height and orientation, the measured data can be compared with those of the multiple reference materials to identify the particular class of objects (e.g., particular production batch, particular color to be colored, and the like) to which it belongs.

Any object of regular shape, such as spherical, cuboidal, tetrahedral, octahedral, prismatic, and the like, or even any irregular shape may be used, provided that it is diamagnetic and of a density that permits its levitation in a magnetic field.

Moreover, the reference and sample material need not necessarily be non-spherical. Even spherical objects can have local density profile differences. As long as there is a visual marker than can be traced and measured, the height and orientation of even spherical objects can be determined.

In some embodiments, the material is a polymer, plastic, wood, paper, fabric, light ceramic, low-density non-magnetic metals, and the like. In certain embodiments, the material is a diamagnetic material having a sufficient density to allow levitation in the applied magnetic field.

In certain embodiments, the magnetic field distribution can be altered using, for example, different magnet geometries, magnet-to-magnet distances, magnetic field strength, and different arrangements of the magnets that can further change the levitation height and orientation of the sample and reference objects. For example, the magnetic field strengths may be diffused by separating the magnets further apart. Use of rectangular, circular, square magnets, or magnets of any shape, can further change the lateral magnetic field distribution. Non-parallel orientation of the magnet faces can alter the magnetic field distribution further. All of these changes in the magnetic field can change the height and orientation of the sample and reference objects as the magnetic field distribution and minimum can affect the objects' interaction with the gravitational field, thereby altering the levitation height and the torque applied (i.e., orientation). Complicated magnetic field distributions can be simulated using a commercial software such as COMSOL. Alternatively, without knowing the precise magnetic field distribution, experiments can be carried out following certain trends (e.g., increasing magnet-to-magnet distribution spreads out the magnetic field along the z-axis) to observe the change in height and orientation of the reference material to compare against the height and orientation of the sample material.

In certain embodiments, rather than changing the magnetic field distribution, the gravitational field relative to the magnetic field distribution can be altered to further affect the levitation height and orientation of the reference and sample material. For example, by tilting the MagLev device, the z-axis can become non-parallel to the direction of gravity and the objects can levitate the materials in entirely different height and orientation. Again, the objects can levitate and orient according to the principle that the sum of all torque and forces experienced by the object is zero.

Such alterations in the magnetic field distribution or gravitational field distribution can alter the height and orientation of the sample and reference material, providing yet another level of quality control in addition to the first comparison. For example, if without a tilt of the MagLev device, the differences in height and orientation of the sample and references materials are near a predetermined error limit, a second quality control can be carried out after tilting the MagLev device in one or more directions. If all of the differences measured are within a predetermined error limit, then the sample material may be accepted as passing a quality control. However, if the differences measured fall outside a predetermined error limit in one or more of these tests, the sample material may be rejected as failing a quality control.

In certain embodiments, a plurality of reference materials can be utilized to compare against the sample material. By obtaining the height and orientation of the sample material with a particular height and orientation of the reference material, further information can be obtained, such as product production batch, material composition of the sample material, and the like.

In certain embodiments, the choice of paramagnetic solution can be altered to provide different buoyancy force and/or different magnetic field distributions within the paramagnetic solution. A paramagnetic salt is added to form the paramagnetic solution. Aqueous or organic solutions of magnetic inorganic salts may be used. Exemplary salts include salts based on the lanthanide cations, manganese (II) chloride, manganese (II) sulfate, iron (II) chloride, iron (II) sulfate, gadolinium (III) chloride, gadolinium (III) chelate salts and the like. The magnetic susceptibility of the paramagnetic organic salt solutions is approximately proportional to concentration. The spatial displacement leading to tilting depends, in part, on the density of the materials to be separated, the density of the supporting solution, the magnetic susceptibility of the paramagnetic salt, along with the constant gradient ($\partial B_z/\partial z$) of the magnetic system used. The closer the density of the paramagnetic solution matches the densities of the materials to be levitated, the smaller the concentration of magnetic salt that is required for displacement. Similarly, the higher the magnetic susceptibility of the magnetic salts, the less is required to achieve displacement. In typical embodiments, concentrations ranging from 0.05 M-2.0 M are suitable.

In certain embodiments, a gadolinium salt is used. Exemplary $Gd^{3+}$ salts include $GdCl_3$, gadolinium (III) (diethylenetriaminepentaacetic acid) (Gd(DTPA)) and (gadolinium (III) diethylenetriamine triacetic acid tetradecane ($Gd(DT_3)$)). There are at least four characteristics of $Gd^{3+}$ cations that make them useful for detection of density differences: i) they (along with some of the other lanthanide cations) possess the largest magnetic susceptibilities ($\chi=+0.028$ cm$^3$/mol $GdCl_3$) of any ionic species; ii) they permit straightforward visualization of samples because their solutions are colorless; iii) they are compatible with proteins and cells when chelated (e.g., $Gd^{3+}$·DTPA complex); and iv) they have acceptable cost (salts of $Gd^{3+}$ can cost <$0.34/g salt=<$0.80/g $Gd^{3+}$=<$125.8/mol $Gd^{3+}$), and the solutions are reusable.

Since $\chi_p$ is negligible for all diamagnetic materials ($\chi_p \approx 0$), the magnetic force on a diamagnetic object is linearly proportional to the magnetic susceptibility of the paramagnetic solution. $Gd^{3+}$ generates a larger magnetic force for a given concentration of cations and value of applied magnetic field than other transition metal cations. The large magnetic susceptibility of $Gd^{3+}$ (compared, for example, to the susceptibilities of other lanthanide cations), enables the system to levitate particles with greater density for an equal concentration of paramagnetic cations, and/or to levitate a given particle using a lower concentration of paramagnetic ions.

In certain embodiments, the paramagnetic solution can be provided with suitable additives, such as diamagnetic salts, soluble polymers, colloidal suspensions, and the like, that can adjust the density or buoyant force of the paramagnetic solution. Adjustments of the paramagnetic solution with suitable additives can be selected to match the particular sample and reference materials to be levitated, based on the object's density, distribution of density, distribution of volume, and the like.

In certain embodiments, the size of the container containing the paramagnetic solution has sufficient volume so that the object is able to freely move in the applied magnetic field.

Other numerous applications will be readily apparent to one of ordinary skill in the art.

Advantages of MagLev for Quality Control

MagLev exhibits numerous different characteristics that make it particularly attractive as a quality control tool.

First, MagLev is simple. Generating patterns of magnetic field gradient with permanent magnets and measuring the height and orientation is fast and easy.

Second, MagLev can measure the height and orientation of a wide range of materials. For example, even when using a pair of simple, relatively low-field magnets, objects with densities between 1-3 g/cm$^3$ can easily be manipulated; this range includes most organic polymers.

In some other embodiments, MagLev is applicable to soft, fragile, and sticky objects (e.g., liquids, gels, pastes, etc.); such objects are otherwise very difficult to handle. Objects that could not be easily mechanically manipulated to perform quality control checks can now be measured using MagLev in a simple and easy method.

Robotic arms can readily grab and place the sample material between the magnetic fields.

In certain embodiments, multiple components with different sizes, shapes or properties can be measured to obtain a quick and easy way to perform quality control using MagLev.

Additionally, changing the magnetic field can change the position and orientation of all components; a number of components can thus be manipulated in parallel.

In certain embodiments, devices for MagLev can be easily modified to expand the range of structures and objects that can be self-assembled. Devices that generate higher fields and field gradients can be used to self-assemble objects that have a higher density or that have smaller sizes. The magnetic fields can be easily altered, for example, by use of permanent magnets with different shapes, or using soft ferromagnetic-field concentrators, or addition of electromagnets, or series of electromagnets, or certain combinations.

Lastly, external power is not required in many procedures.

EXAMPLES

Experimental Design

The repulsive force exerted by non-uniform magnetic fields on diamagnetic materials is typically negligible for most materials, and is insufficient to suspend them against gravity in air using permanent magnets (bismuth and graphite are exceptions, but the strength of their repulsion from a region of high field is still small compared to the strength of attraction of most paramagnetic objects). A simple strategy for achieving MagLev of diamagnetic objects with permanent magnets is to suspend these objects in a paramagnetic fluid, and to place that fluid in a magnetic field gradient generated using two magnets oriented with like poles facing each other. In this arrangement, the paramagnetic medium is attracted towards the regions of high magnetic field, and displaces the diamagnetic object towards regions of lower magnetic field; this exchange of paramagnetic matter for diamagnetic in regions of high magnetic field enables magnetic levitation.

The NdFeB magnets utilized are inexpensive (~$20 when purchased individually and significantly less in bulk), and generate large magnetic fields (remnant field, $M_R$=1.1 kA/m and field at the magnet surface ~0.4 T). Their large coercivity ($H_C$=1.1 T) makes them resistance to demagnetization when multiple magnets are used in an anti-Helmholtz arrangement. Two rectangular prism-shaped magnets in an anti-Helmholtz configuration generate a region of low magnetic field between the magnets—an oblate-spheroid-shaped "magnetic bottle."

This configuration is especially useful for quality control for several reasons. First, the system centers and aligns levitating diamagnetic objects or clusters along a vertical centerline between the magnets, because the magnitude of the magnetic field is minimal in that region of the x-y plane. Second, it levitates objects that are either more dense or less dense than the paramagnetic solution; objects that are more dense than the medium sink in the absence of the magnetic field, and their levitation is enabled by the bottom magnet; objects that are less dense than the medium float in the absence of an applied magnetic field, and their levitation (or "reverse levitation") is enabled by the top magnet. Third, the magnetic field gradient can be easily altered by changing the distance between magnets.

The paramagnetic solution enables levitation in two ways: i) it provides a buoyant force that counteracts gravity, and ii) it controls the magnitude of the magnetic force experienced by the paramagnetic medium, and thus contributes another force to those experienced by the diamagnetic objects.

Details of the MagLev Device

Permanent NdFeB magnets (Grade N50, shaped as rectangular prisms with dimensions of 2 in×2 in×1 in, supplied by K&J Magnetics) with a surface field of ~0.4 T generated the magnetic field. Some NdFeB magnets (square prisms: grade N50, 2 in×2 in×1 in, Model # NB063-N50; rectangular prisms: grade N42, 4 in×2 in×1 in, Model # NB079) were purchased from Applied Magnets (www.magnet4less.com). The magnets were held at a distance of 20-70 mm (the distance between the magnets could be adjusted) in an anti-Helmholtz arrangement within an aluminum casing. The aluminum casing for the magnets was designed and fabricated by Gaudreau Engineering (West Warwick, R.I.) for a fee.

Example 1

Quality Control for Plastic Injection-Molded Parts Using Magnetic Levitation

Figure 3:
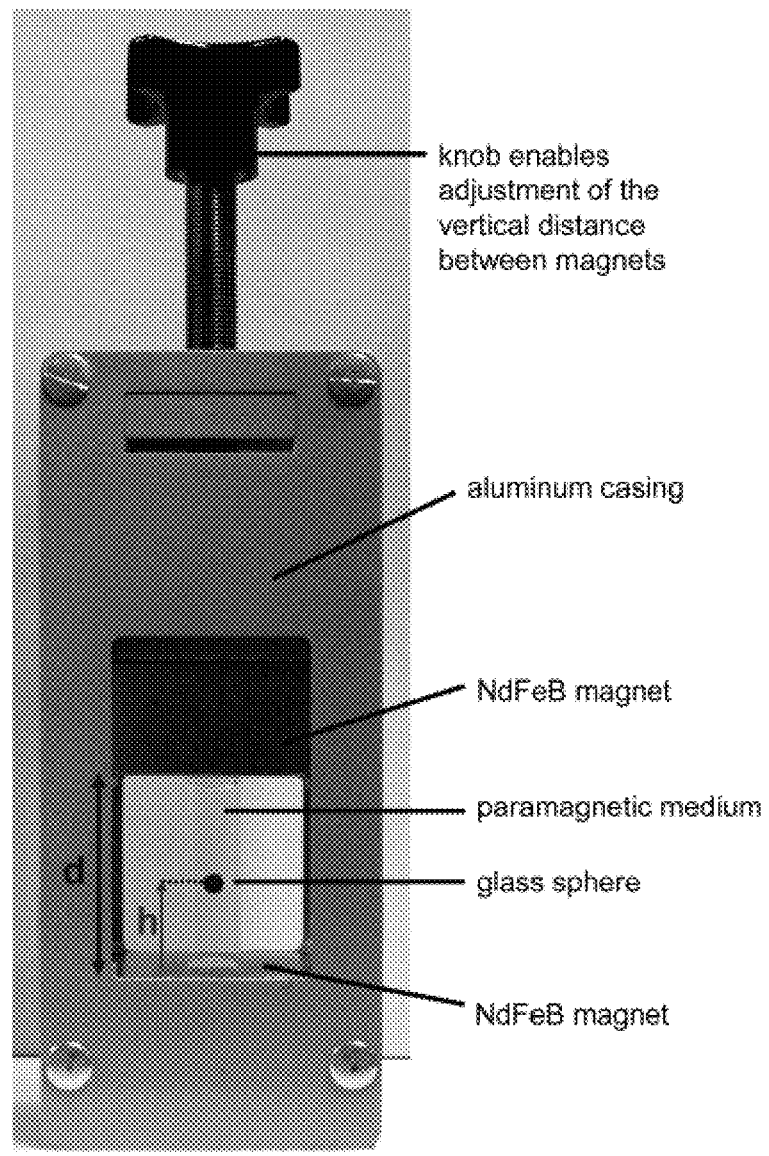
FIG. 3 shows a photograph of the MagLev device in accordance with certain embodiments.

FIG. 3 shows a MagLev device utilized for the experiments. Objects to be levitated are placed within a container of paramagnetic medium and levitate at height h above the surface of the bottom magnet when positioned in the device. The distance d between the magnets can be easily adjusted by turning the knob attached to the device.

Nylon screws of various types were levitated in the MagLev device shown in FIG. 3. Nylon is a hard plastic having a density of 1.15 g/cm$^3$ and was readily available at local hardware stores. The magnets in the device were separated by d=45 mm. Between experiments, the container with the screw was removed from the device, and the medium and screw were lightly stirred and agitated by hand using a set of tweezers. In each experiment, the screw adopts one of four orientations in which the length of the screw is aligned with the diagonal of the square face of the magnet.

Figure 4A:
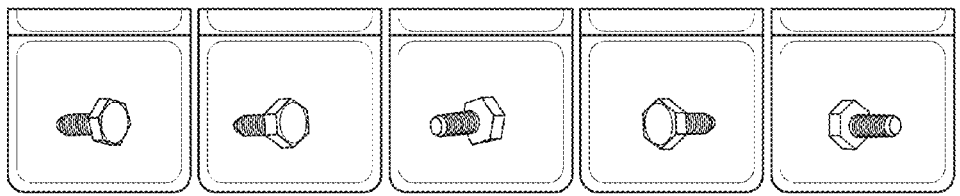
FIGS. 4A and 4B shows photographs of two different nylon hex cap screws levitating in a paramagnetic solution in accordance with certain embodiments.
Figure 4B:
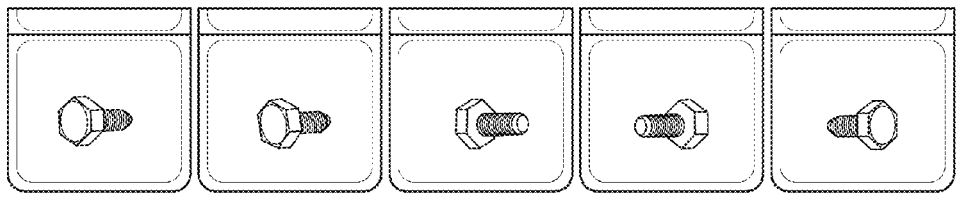

FIG. 4 shows five repeat experiments for two different ¼-20 nylon hex cap screws (length=½") (top and bottom) of the same size acquired from the same manufacturer, presumably from the same batch, levitating in 1.3M MnCl$_2$. The magnets in the device were separated by d=45 mm. Each row shows five repeat experiments for a given screw. Between experiments, the container with the screw was removed from the device, and the medium and screw were lightly stirred and agitated by hand using a set of tweezers.

As shown, in each experiment, the screw adopts one of four orientations in which the length of the screw is aligned with the diagonal of the square face of the magnet. The screws levitate at the same height in each experiment; the orientation of the screw varies slightly from experiment-to-experiment, due to the four-fold symmetry of the square prism magnets. Repeated measurements for a single object shows the reliability of MagLev to consistently yield the same results for a particular object.

The similarity in levitation height and orientations for the two screws shown here suggests that the screws are similar in material composition (they have the same density) and shape.

Figure 5A:
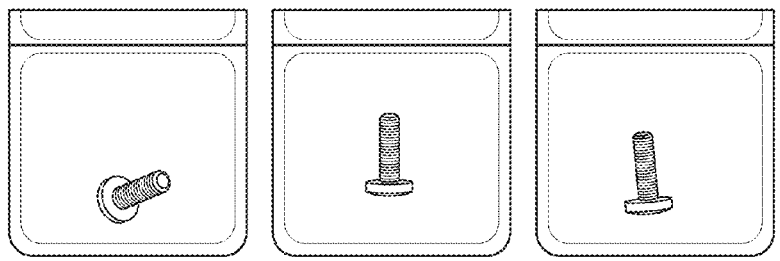
FIGS. 5A and 5B shows photographs of 12 mm-long nylon screws levitating in a paramagnetic solution where differences in the shape and/or distribution of density are observed as differences in height and orientation in accordance with certain embodiments.
Figure 5B:
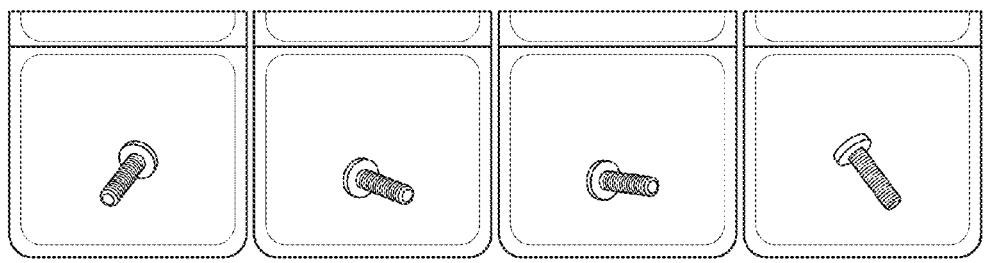

FIG. 5 shows several images of 12-mm long individual slotted-head nylon screws of two different sizes (top=8-32; bottom=6-32) levitating in ~1 M MnCl$_2$. Each photograph shows a different screw. These screws were acquired from a local hardware store, and differed visibly in coloration, suggesting that they were not from the same batch. Differences across screws when levitating in the MagLev device were observed both in their levitation height, and in orientation, suggesting that these screws had different material properties (different density) and possibly slight differences in shape. Differences in the material composition (density) of the screws is observed as differences in levitation height. Differences in the shape and/or distribution of density in the screw is observed as differences in orientation.

As shown, for a given set of conditions (e.g., concentration of the paramagnetic medium, distance between the magnets, shape of the magnets), MagLev reliably and repeatedly levitates objects at a given height and in a particular orientation. Objects from different packages can levitate at different heights, denoting differences in batch processing. Observable differences between the levitation characteristics of different objects may be considered a novel metric for quality control.

What is claimed is:

1. A method for performing a quality control of a diamagnetic sample material, comprising:
    levitating a diamagnetic sample material having a non-uniform density profile in a paramagnetic solution using a magnetic field to attain a position and orientation at static equilibrium;
    identifying the position and orientation at static equilibrium of said sample material in the paramagnetic solution;
    comparing the identified position and orientation at static equilibrium of said sample material to an identified position and orientation at static equilibrium of a reference material; and
    determining whether differences between the identified position and orientation at static equilibrium of the sample material and the identified position and orientation at static equilibrium of the reference material are within a predetermined range.

2. The method of claim 1, further comprising:
    providing a first paramagnetic solution comprising a paramagnetic material in a solvent;
    providing a reference material having a reference density and a reference density profile in said first paramagnetic solution;
    applying a magnetic field to the first paramagnetic solution;
    measuring a position and orientation at static equilibrium of said reference material in the first paramagnetic solution.

3. The method of claim 1, wherein the reference material and the sample material have a non-spherical geometry.

4. The method of claim 1, wherein the reference material and the sample have a spherical geometry with a visual marker to detect orientation in the first and second paramagnetic solutions.

5. The method of claim 1, wherein the reference density and the reference density profile of the reference material is known.

6. The method of claim 1, wherein the sample material comprises components from a mechanical device.

7. The method of claim 1, wherein a plurality of reference materials are provided.

8. The method of claim 1, further comprising identifying sample materials that have differences that are greater than the predetermined range as failing the quality control.

9. The method of claim 1, further comprising identifying sample materials that have differences that are equal to or smaller than the predetermined range as passing the quality control.

10. The method of claim 1, wherein the orientations are measured relative to at least one axis of a Cartesian coordinate system.

* * * * *